United States Patent [19]
Kato et al.

[11] Patent Number: 6,054,098
[45] Date of Patent: Apr. 25, 2000

[54] APPARATUS FOR MEASURING OZONE

[75] Inventors: Junji Kato; Toshikazu Ohnishi, both of Minami-ku, Japan

[73] Assignee: Horiba, Ltd., Kyoto, Japan

[21] Appl. No.: 09/122,537

[22] Filed: Jul. 24, 1998

[30]    Foreign Application Priority Data

Jul. 28, 1997  [JP]  Japan ................................. 9-218125

[51] Int. Cl.[7] ............................................. G01N 7/00
[52] U.S. Cl. ............................ 422/83; 422/93; 436/135; 436/155; 436/158; 436/159
[58] Field of Search ................. 422/83, 93; 436/135, 436/155, 158, 159

[56]         References Cited
         U.S. PATENT DOCUMENTS 3,464,797   9/1969   Hagopian .

*Primary Examiner*—Jan Ludlow
*Attorney, Agent, or Firm*—Oppenheimer Wolff & Donnelly LLP

[57]           ABSTRACT

This invention provides an apparatus for measuring ozone in which interference effects of $SO_2$ are intended to be reduced. This invention comprises a reference gas line for generating reference gas with ozone removed by allowing the sample gas to pass through the ozone decomposer with silver wool used as a catalyst, a sample gas line for introducing the sample gas as it is, an ozone analyzer to which the reference gas line and the sample gas line are connected via a selector valve and which measures the ozone component in the sample gas by introducing the reference gas and the sample gas alternately at specified intervals, and a temperature controller installed to the ozone decomposer for setting the catalyst reaction temperature to a range from 100 to 130° C.

2 Claims, 1 Drawing Sheet

APPARATUS FOR MEASURING OZONE

BACKGROUND OF THE INVENTION

1. Field of the Invention

The present invention relates to an apparatus for measuring ozone component in the sample gas.

2. Description of the Prior Art

In the ozone measuring apparatus configured to determine the ozone component by the subtraction method by connecting the reference gas line for introducing reference gas with ozone removed by allowing the gas to pass the ozone decomposer and a sample gas line for introducing the sample gas as it is to an ozone analyzer via a selector valve and by introducing the reference gas and the sample gas alternately at specified intervals from both lines, there is an advantage of little interference effects because interference components are canceled each other.

For the above-mentioned ozone decomposer, various oxidation catalysts are used, but for example, when silver wool is used, the ozone decomposer is usually heated to about 170° C. for reducing the interference caused by $H_2O$ in the atmosphere for application.

However, at this level of temperature, oxidation reactions shown by

$$Ag + O_2 \rightarrow AgO + \frac{1}{2} O \qquad \text{Eq. (1)}$$

and reduction reactions shown by

$$AgO \rightarrow Ag + \frac{1}{2} O \qquad \text{Eq. (2)}$$

take place, but the oxidation reaction of Eq. (1) is more conspicuous than the reduction reaction of Eq. (2), and adsorption of $SO_2$ component occurs on the AgO surface.

Because there is a portion in which $SO_2$ ultraviolet ray absorption spectrum overlaps ultraviolet ray absorption of ozone, if the $SO_2$ component is contained in the sample gas, $SO_2$ may be adsorbed to the ozone decomposer, causing a concentration difference of $SO_2$ between reference gas and sample gas, and $SO_2$ interference effects occur.

SUMMARY OF THE INVENTION

Under these circumstances, it is an object of this invention to provide an apparatus for measuring ozone in which interference effects of $SO_2$ are intended to be reduced.

This invention configures the means for solving the above problems in the following manner.

That is, this invention comprises a reference gas line for generating reference gas with ozone removed by allowing the sample gas to pass through the ozone decomposer with silver used as a catalyst, a sample gas line for introducing the sample gas as it is, an ozone analyzer to which the reference gas line and the sample gas line are connected via a selector valve and which measures the ozone component in the sample gas by introducing the reference gas and the sample gas alternately at specified intervals, and a temperature control means installed to the ozone decomposer for setting the catalyst reaction temperature to a range from 100 to 130° C.

Since ozone decomposes at temperature of 100° C. or higher, $SO_2$ interference can be reduced by setting conditions in which temperature is 100° C. or higher and $SO_2$ interference is slight. FIG. 3 is a graph showing catalyst reaction temperature and $SO_2$ interference, which indicates that the $SO_2$ interference is a little in the temperature range from 100 to 130° C., suggesting that the catalyst should be reacted in this temperature range.

DETAILED DESCRIPTION OF THE INVENTION

Figure 1:
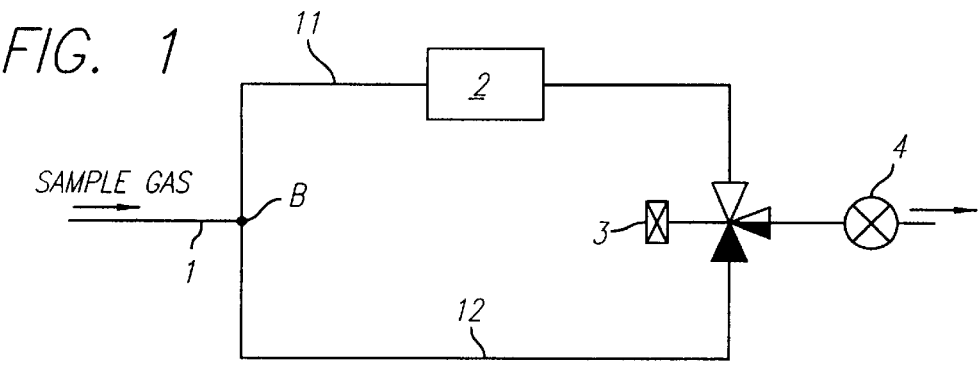
FIG. 1 is a block diagram showing one embodiment of the apparatus for measuring ozone according to this invention.

Referring now to the drawings, a preferred embodiment of the apparatus for measuring ozone according to the invention will be described in detail hereinafter.

FIG. 1 shows a configuration of the apparatus for measuring ozone using the ultraviolet ray absorption method, and numeral 1 designates a sample introducing line for introducing the sample gas, and the sample introducing line 1 branches into a reference gas line 11 and a sample gas line 12 at the branching point B, and to the reference gas line 11, an ozone decomposer 2 using silver wool as a catalyst is installed and ozone in the sample gas is removed to generate reference gas, while to the sample gas line 12, sample gas is introduced as it is, and the reference gas line 11 and the sample gas line 12 are connected to the ozone analyzer 4 using the ultraviolet ray absorption method via a three-way selector valve 3, and the reference gas and sample gas are introduced into the ozone analyzer 4 alternately at specified intervals.

Figure 2:
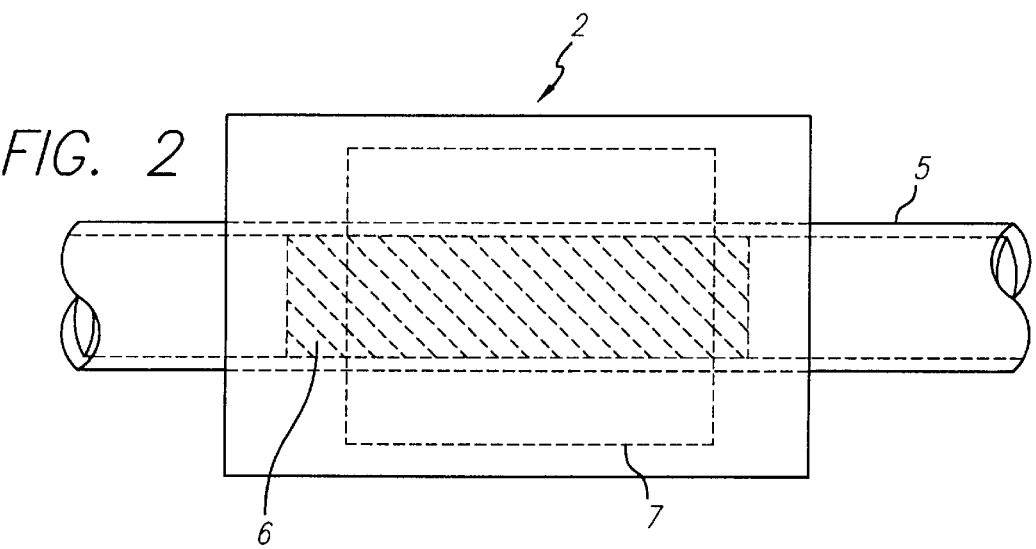
FIG. 2 is a block diagram of the ozone decomposer.

The configuration of the above ozone decomposer 2 is shown in FIG. 2, and numeral 5 designates a glass tube, 6 silver wool as catalyst packed in the glass tube 5, and 7 a heater block (temperature control means), for which for example, positive temperature characteristic thermister with self-temperature control capabilities or various cartridge heaters are used, and whose temperature is set to 100 to 130° C. so that the interference effects of $SO_2$ component can be suppressed.

Figure 3:
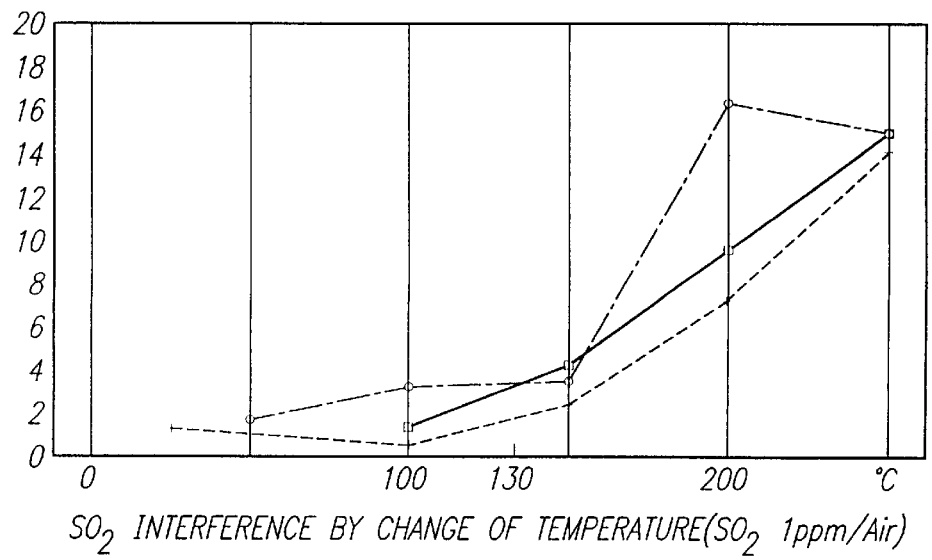
FIG. 3 is a graph showing the relationship between the catalyst reaction temperature and $SO_2$ interference effects in the ozone decomposer.

FIG. 3 is a graph showing the relationship between the catalyst reaction temperature and $SO_2$ interference, and in this case, three measured values for determining the concentration difference (between reference gas line 11 and sample gas line 12) due to adsorption of $SO_2$ component at each temperature are shown with □, +, and ○ marks connected with solid line, broken line, and alternate long and short dash line, respectively, indicating that in the temperature range from 100 to 130° C., adsorption of $SO_2$ component to the surface of oxidized silver wool (AgO) is slight. Because ozone decomposes at 100° C. or higher, the above temperature range is set as a condition in that $SO_2$ adsorption is slight in the temperature range of 100° C. to 130° C.

As described above, because the catalyst reaction temperature is set to a temperature range from 100 to 130° C. in the apparatus for measuring ozone using the ozone decomposer with silver used as a catalyst, adsorption of $SO_2$ component to the oxidized silver surface is able to be held slight and $SO_2$ interference effects can be reduced and suppressed.

What is claimed is:

1. An apparatus for measuring ozone comprising a reference gas line for generating reference gas with ozone removed by allowing the sample gas to pass through the ozone decomposer with silver used as a catalyst, a sample gas line for introducing the sample gas as it is, an ozone analyzer to which the reference gas line and the sample gas line are connected via a selector valve and which measures the ozone component in the sample gas by introducing the reference gas and the sample gas alternately at specified intervals, and a temperature control means installed to the ozone decomposer for setting the catalyst reaction temperature to a range from 100 to 130° C.

2. An apparatus for measuring ozone according to claim 1, in which the catalyst is silver wool.

* * * * *